United States Patent
Humphrey (10) Patent No.: US 9,884,208 B2
(45) Date of Patent: Feb. 6, 2018

(54) POSITION DETERMINATION

(71) Applicant: Reflex Imaging Limited, Horsham, West Sussex (GB)

(72) Inventor: Malcolm Humphrey, Horsham (GB)

(73) Assignee: REFLEX IMAGING LIMITED, Horsham, West Sussex (GB)

(*) Notice: Subject to any disclaimer, the term of this patent is extended or adjusted under 35 U.S.C. 154(b) by 178 days.

(21) Appl. No.: 14/425,273

(22) PCT Filed: Sep. 2, 2013

(86) PCT No.: PCT/GB2013/000366
§ 371 (c)(1),
(2) Date: Mar. 2, 2015

(87) PCT Pub. No.: WO2014/033425
PCT Pub. Date: Mar. 6, 2014

(65) Prior Publication Data
US 2015/0265853 A1    Sep. 24, 2015

(30) Foreign Application Priority Data

Aug. 31, 2012  (GB) .................................. 1215560.2
Sep. 18, 2012  (GB) .................................. 1216604.7

(51) Int. Cl.
*G01B 11/14*  (2006.01)
*A61N 5/10*   (2006.01)
(Continued)

(52) U.S. Cl.
CPC ............ *A61N 5/1049* (2013.01); *A61B 90/39* (2016.02); *A61N 5/1048* (2013.01); *G01S 1/70* (2013.01);
(Continued)

(58) Field of Classification Search
CPC ...... A61N 2005/105; A61N 2005/1059; A61N 5/10; A61N 5/1045; A61N 5/1048;
(Continued)

(56) References Cited

U.S. PATENT DOCUMENTS

| | | |
|---|---|---|
| 4,788,441 A | 11/1988 | Laskowski |
| 4,936,678 A | 6/1990 | Gordon et al. |

(Continued)

FOREIGN PATENT DOCUMENTS

| | | |
|---|---|---|
| BE | 1008234 A5 | 2/1996 |
| EP | 0314231 A2 | 10/1988 |

(Continued)

OTHER PUBLICATIONS

"Dual-Axis Analog MEMS Pointing Mirror." (2004); Texas Instruments. Web. http://www.ti.com/lit/ds/symlink/talp1000b.pdf.

(Continued)

*Primary Examiner* — Tri T Ton
(74) *Attorney, Agent, or Firm* — David D. Brush; Westman Champlin & Koehler, P.A.

(57) ABSTRACT

An apparatus for position-detection of an object within a region is disclosed. The apparatus includes first and second target elements mounted on an object and having a known separation distance between the two. A scanning light source is configured to issue a beam of light along a substantially one-dimensional scanning path, which illuminates a point that moves over the first and second target elements. A detector is provided for detecting light reflected from, or received by, the first and second target elements. A processing system is configured to determine the position of the object within the region based on first and second points in the scanning path at which the detector detects light returned (Continued)

from, or received by, the first and second target elements and the known separation distance between the two reflective elements.

16 Claims, 8 Drawing Sheets

(51) Int. Cl.
*G01S 17/06* (2006.01)
*G01S 1/70* (2006.01)
*G01S 7/481* (2006.01)
*G01S 17/48* (2006.01)
*A61B 90/00* (2016.01)
*G01S 5/16* (2006.01)

(52) U.S. Cl.
CPC ............ *G01S 7/4817* (2013.01); *G01S 17/06* (2013.01); *G01S 17/48* (2013.01); *A61B 2090/3937* (2016.02); *A61N 5/10* (2013.01); *A61N 5/1045* (2013.01); *A61N 2005/105* (2013.01); *A61N 2005/1059* (2013.01); *G01S 5/16* (2013.01)

(58) Field of Classification Search
CPC ....... A61N 5/1049; G01S 17/06; G01S 17/48; G01S 1/70; G01S 5/16; G01S 7/4817; A61B 19/54; A61B 2019/5437; A61B 2090/3937
USPC .................................................. 356/614–625
See application file for complete search history.

(56) References Cited

U.S. PATENT DOCUMENTS

| | | |
|---|---|---|
| 5,734,476 A | 3/1998 | Dlugos |
| 6,115,114 A | 9/2000 | Berg et al. |
| 7,924,441 B1 | 4/2011 | Milanovic |

FOREIGN PATENT DOCUMENTS

| | | |
|---|---|---|
| EP | 2085117 A1 | 8/2009 |
| WO | 2011107112 A1 | 9/2011 |

OTHER PUBLICATIONS

International Search Report dated May 21, 2014 for corresponding International Application No. PCT/GB2013/000366, filed Sep. 2, 2013.

Veljko Milanovic et al., "Fast and High-Precision 3D Tracking and Position Measurment with MEMS Micromirrors", 2008 IEEE/LEOS International Conference on Optical MEMS and Nanophotonics, Aug. 1, 2008 (Aug. 1, 2008), pp. 72-73, XP055021111.

Written Opinion of the International Searching Authority dated Feb. 28, 2015 for corresponding International Application No. PCT/GB2013/000366, filed Sep. 2, 2013.

Great Britain Search Report dated Nov. 27, 2012 for corresponding GB Application No. 1216604.7, filed Sep. 18, 2012.

POSITION DETERMINATION

CROSS-REFERENCE TO RELATED APPLICATION

This application is a Section 371 National Stage Application of International Application No. PCT/GB2013/000366, filed Sep. 2, 2013, which is incorporated by reference in its entirety and published as WO 2014/033425 on Mar. 6, 2014, in English.

FIELD OF THE INVENTION

This invention relates to an apparatus and method for position determination.

BACKGROUND OF THE INVENTION

It is known to determine the position of an object using optical metrology, which includes the process of using reflected light to identify or at least estimate the position of an object in a region.

Optical metrology is one way of obtaining the real-time position of a moving object, for example in gaming, robotics, human-computer interaction applications and in medical applications. Regarding the latter, optical metrology has been found to be particularly useful in radio therapeutic apparatuses where it is important to determine the position of a remote object with a high degree of accuracy. One example is that of a multi leaf collimator (MLC) which is a device used in a linear accelerator (Linacs) to shape a beam of X-ray radiation to appropriately treat tumours. The position of each leaf must be accurately determined but from a remote position to avoid exposure to the X-rays. The use of a scanning light source and reflectors for identifying the leaf positions has been described in WO2011/107112.

A fast and accurate three-dimensional (3D) tracking and position measurement method is described in http://adriaticresearch.org/Research/pdf/Tracking_OMEMS2008.pdf.

Here, two sets of two-dimensional (2D) micro-electromechanical (MEM) scanning mirrors are required to track an object in 3D space, regardless of the method used to mark the devices to the system, e.g. using reflectors or infra-red (IR) sources. However, 2D MEM devices are relatively expensive, particularly compared with one-dimensional (1D) MEM devices and furthermore require additional circuitry to drive and track their orientation.

SUMMARY OF THE INVENTION

A first aspect of the invention provides apparatus for position-detection of an object within a region, the apparatus comprising: first and second target elements mounted or mountable on an object and having a known separation distance between the two; a scanning light source adapted to issue a beam of light along a substantially one-dimensional scanning path which illuminates a point that moves over the first and second target elements; detection means for light reflected from, or received by, the first and second target elements; and processing means configured to determine the position of the object within the region based on first and second points in the scanning path at which the detection means detects light returned from, or received by, the first and second target elements and the known separation distance between the two reflective elements.

The first and second target elements may be reflective elements. Said reflective elements may be retroreflective elements. Alternatively, the first and second target elements may be photodetector elements.

The processing means may be configured to determine the position of the object based on respective first and second angles between a reference position and the positions of said first and second points in the scanning path, and the known separation distance between the two reflective elements.

The processing means may be configured to determine the first and second angles using optical feedback to directly measure the angle at which the scanning light source is emitting its beam when a reflection from a reflective element is detected at the detector.

Alternatively, the apparatus may further comprise one or more reference reflectors located at known position(s) within the region covered by the scanning path and wherein the processing means is configured to determine the first and second angles based on the respective positions of said first and second points relative to reference point(s) in the scanning path at which the detector detects light returned from the or each reference reflector.

The processing means may be configured to determine an indication of at least the object's distance from the light source along a first dimensional axis by means of triangulation based on the first and second angles and the known separation distance between the two reflective elements. The processing means may be further configured to generate an indication of the of the object's relative position along a second dimensional axis, generally orthogonal to the first.

The scanning light source may comprises a source of light and a mirror, the source of light being directed towards the mirror, the mirror being controllably movable so as to direct light from the source towards the object along the one-dimensional scanning pattern. The source of light may be a laser. The mirror may be part of a micro-electromechanical (MEM) device with associated control means. The detector is configured so as to receive the reflected light from the controllably movable mirror.

The processing means may be configured to determine the first and second angles using optical or electrical feedback to directly measure the angle of the mirror when a reflection from a reflective element is detected at the detector.

The processing means may be configured to determine the first and second angles using the time taken between detecting a reflection between a reference mirror and from the respective first and second reflective elements.

One of the reflective elements, or a further reflective element, may be provided having a property or characteristic that causes a temporal variation in reflected light depending on the part of the element that is illuminated along a given axis, and wherein the processing means is further configured to determine the position of the object based on the reflected light received by the detector from said reflective element. Said reflective element may have a shape that varies in width along the given axis, substantially transverse to the one-dimensional scanning path, and wherein the processing means is further configured to determine the position of the object based on the width of the light pulse received by the detector from said reflective element. Said reflective element may have a shape that tapers inwards along the given axis.

The first and second target elements may be photodetectors which comprise the detection means.

A second aspect of the invention provides apparatus for position-detection of an object within a region, the apparatus comprising: first and second reflective elements mounted or mountable on an object and having a known separation distance between the two; a scanning light source which includes a mirror adapted to be controllably movable so as to direct emitted light towards the object, back-and-forth along a one-dimensional scanning path to illuminate a point that moves over the first and second reflective elements; a detector for generating a signal indicative of light reflected from the first and second reflective elements; and processing means configured to determine the position of the object along first and second axes within the region by means of determining using the light signal (i) first and second angles between a reference point and the position of the mirror at which light is reflected from the first and second reflective elements and (ii) the known separation distance between the two.

One of the first and second reflective elements, or a third reflective element, may be provided and configured so as to vary in shape along an axis substantially transverse to that of the scan path thereby to cause a temporal variation in the light signal depending on the part of the element along said transverse axis that is illuminated, and wherein the processing means is further configured to determine the position of the object along said transverse axis based on said light signal.

A third aspect of the invention provides apparatus for position-detection of an object within a region, the apparatus comprising: a reflective element mounted or mountable on an object; a scanning light source adapted to issue a beam of light back-and-forth along a substantially one-dimensional scanning path which illuminates a point that moves over the reflective element; a detector for generating a signal in response to light reflected from the reflective element; and processing means configured to determine the position of the object within the region based on the light signal, wherein the reflective element has a property or characteristic that causes a variation in the reflected light signal depending on which part of the element is illuminated along the axis substantially transverse to the scanning path, and wherein the processing means is further configured to determine the object's position along said axis based on the light signal.

Preferred features of this aspect are defined in the appended claims. For examples, the apparatus may be employed in radiotherapeutic apparatus.

A fourth aspect of the invention provides a method for position-detection of an object within a region, the method comprising: scanning a beam of light along a substantially one-dimensional scanning path which illuminates a point that moves over first and second target elements mounted on an object separated by a known distance; detecting light reflected from, or received by, the first and second reflective elements; and determining the position of the object within the region based on first and second points in the scanning path at which the detector detects light returned from, or received by, the first and second target elements and the known separation distance between the two.

Preferred features of this aspect are defined in the appended claims.

A fifth aspect of the invention provides a method for position-detection of an object within a region, the method comprising: controlling a mirror so as to scan a beam of light back-and-forth along a substantially one-dimensional scanning path which illuminates a point that moves over first and second reflective elements mounted on an object separated by a known distance; detecting light reflected from the first and second reflective elements and generating a signal indicative of the detected light; determining the position of the object along first and second axes within the region by means of determining using the light signal (i) first and second angles between a reference point and the position of the mirror at which light is reflected from the first and second reflective elements and (ii) the known separation distance between the two.

A sixth aspect of the invention provides a method for position-detection of an object within a region, the method comprising: scanning a beam of light along a substantially one-dimensional scanning path which illuminates a point that moves over a reflective element mounted on an object separated by a known distance, the reflective element having a property or characteristic that causes a variation in the reflected light signal depending on which part of the element is illuminated along the axis substantially transverse to the scanning path; detecting light reflected from the reflective element; and generating a signal indicative of said detected light; and determining the position of the object within the region based on the light signal.

Preferred features are defined in the appended set of claims.

A seventh aspect of the invention provides a non-transitory computer-readable storage medium having stored thereon computer-readable code, which, when executed by computing apparatus, causes the computing apparatus to perform a method comprising: scanning a beam of light along a substantially one-dimensional scanning pattern which illuminates a point that moves over first and second target elements mounted on an object separated by a known distance; detecting light reflected from, or received by, the first and second target elements; and determining the position of the object within the region based on first and second points in the scanning pattern at which the detector detects light returned from, or received by, the first and second target elements and the known separation distance between the two.

An eighth aspect of the invention provides an apparatus, the apparatus having at least one processor and at least one memory having computer-readable code stored thereon which when executed controls the at least one processor: to scan a beam of light along a substantially one-dimensional scanning pattern which illuminates a point that moves over first and second target elements mounted on an object separated by a known distance; to detect light reflected from, or received by, the first and second target elements; and to determine the position of the object within the region based on first and second points in the scanning pattern at which the detector detects light returned from, or received by, the first and second reflective elements and the known separation distance between the two.

A ninth aspect of the invention provides apparatus for position-detection of an object within a region, the apparatus comprising: first and second light sources, for example IR light sources, mounted or mountable on an object and having a known separation distance between the two; light detection means; a scanning reflector adapted to move along a substantially one-dimensional scanning path so as to reflect light from each of the first and second light sources to the light detection means at respective first and second points in the scanning path; and processing means configured to determine the position of the object within the region based on the first and second points in the scanning path at which the detection means detects light from the first and second light sources and the known separation distance between the two light sources.

A tenth aspect of the invention provides method for position-detection of an object within a region, the method comprising: emitting light from first and second light sources, IR sources for example, which are positioned on an object with a known separation distance between the two;

scanning a reflector along a substantially one-dimensional scanning path to reflect light from each of the first and second light sources; detecting first and second points in the scanning path when light from the respective light sources is reflected into a light sensor; and determining the position of the object within the region based on the first and second points in the scanning path at which light is detected from the first and second light sources and the known separation distance between the two light sources.

BRIEF DESCRIPTION OF THE DRAWINGS

Embodiments of the invention will now be described by way of non-limiting example with reference to the accompanying drawings, in which.

DETAILED DESCRIPTION OF PREFERRED EMBODIMENTS

The following embodiments describe a system and method for position determination of an object within a space or region. The systems and method are applicable to the medical instruments field, for example in radiotherapy whereby the position of certain objects (e.g. the leaves of a MLC) need to be determined accurately and remotely from the radiation source. The systems and methods are however applicable in any field or application in which position determination is required.

In some embodiments, the system and method operate by means of directing a beam of light along a one-dimensional path only, for example from side-to-side along a single axis (although in practice any orientation can be used and there may be slight deviations either side of this axis). Consequently the scanning apparatus, which in the embodiments below include an oscillating MEM mirror, can use a one-dimensional device offering advantages in terms of relative cost and complexity. Even if a two-dimensional device is used, operating it in a one-dimensional mode still offers simplicity in terms of the controlling electronics and signal processing.

In another embodiment, the MEM mirror works in the same way but reflects light transmitted from the object towards a sensor. Again, the same advantages of simplicity and cost are provided.

Furthermore, only a single scanning apparatus is needed unlike some prior art systems.

Furthermore, as the embodiments below will explain, a single, one-dimensional scan can be used to determine the position in three dimensions whereas prior art systems require two-dimensional scanning. Consequently, the overall refresh rate (the number of times per second the position can be determined) could be many orders of magnitude higher than with prior art methods.

Position determination in the present context involves obtaining measurement data representing the distance of the object, or part thereof, from a reference position. Subsequent processing can be used to convert the obtained measurement (s) into coordinates or a vector representing an absolute position within 2D or 3D space.

It will be appreciated that by repeating the position determination steps periodically for subsequent scans enables movement to be detected and captured which may involve, for example, recording and/or plotting the movement path of an object in a region.

In the first embodiment, there is provided an apparatus for the measurement of an object's longitudinal and lateral distance from a reference position. In the second embodiment, an additional measurement is generated indicative of the object's vertical displacement from a reference position. The terms longitudinal, lateral and vertical are relative ones used for ease of reference. Other position representations can be derived.

The apparatuses described can be used to obtain the position in one, two or three dimensions.

Figure 1:
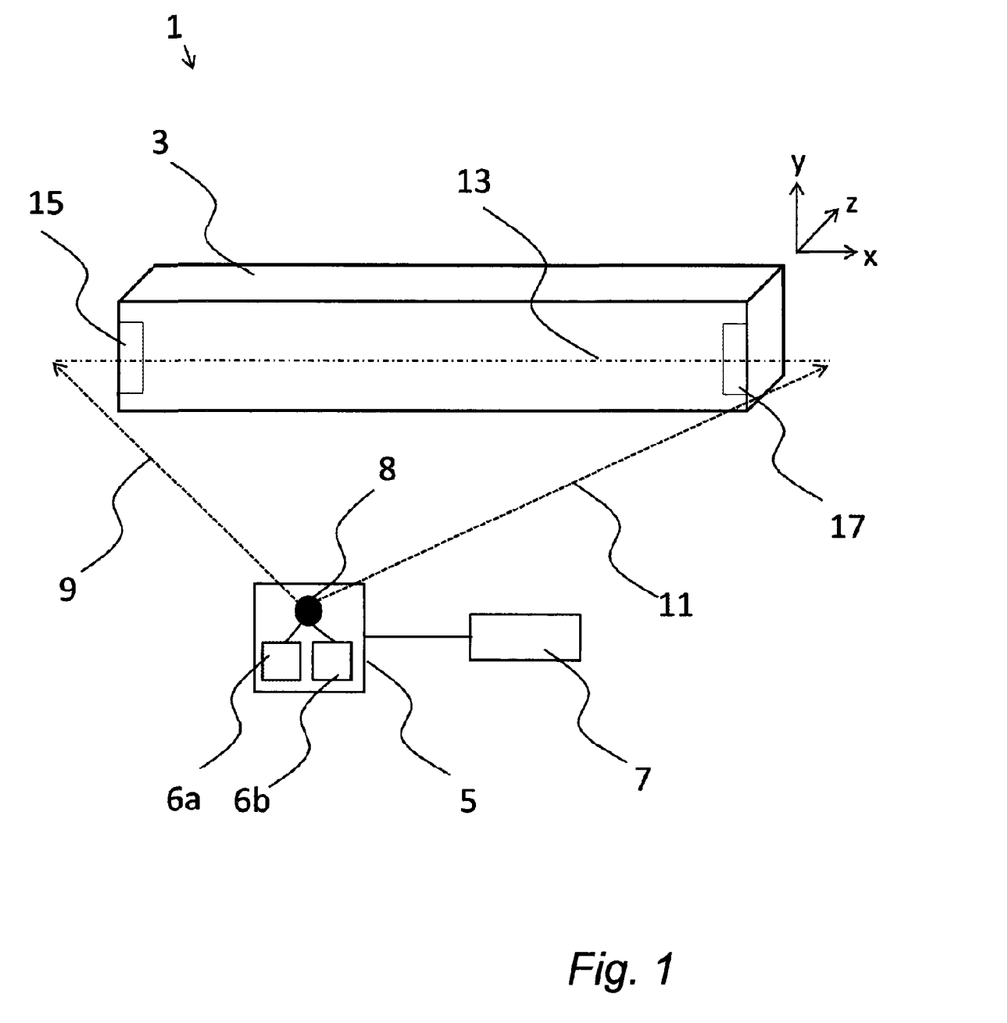
FIG. 1 is a schematic diagram of a first embodiment position determining apparatus according to the invention.

Referring to FIG. 1, a first embodiment apparatus 1 is shown for determining the position of an object 3, particularly its longitudinal and/or lateral position or displacement. Orthogonal x, y and z axes are shown and longitudinal and lateral positions refer to positions along the z and x axes respectively.

The apparatus 1 comprises a scanning system 5 incorporating a one-dimensional MEM mirror 8, a laser light source 6a and a light detector 6b. The laser light source 6a is arranged to direct a beam of light towards the MEM mirror 8 which reflects the beam towards the object 3. The light detector 6b is arranged to detect light reflected back via the MEM mirror 8. The light detector 6b can be positioned in front of the MEM mirror 8 or before it and in both cases a beam splitter can be used, as is the case of the third embodiment below. A processing system 7 is associated with the scanning system 5 and operates under software control to serve the dual purpose of (a) controlling the angle of the MEM mirror 8, and (b) processing the received signal from the light detector 6b to perform position determination.

More specifically, the processing system 7 is programmed or otherwise configured to move the MEM mirror 8 back and forth along a predefined one-dimensional axis thereby defining a scan pattern, or more appropriately, path for the laser beam which is indicated in FIG. 1 by the dashed line 13. Reference numerals 9 and 11 indicate extremities of the scan path 13 although these can be wider or narrower.

The apparatus 1 further comprises first and second reflectors 15, 17 which are fixed to the object with a predefined separation distance s between the two. Each reflector 15, 17 is a retro-reflector. The arrangement of the MEM mirror 8 and reflectors 15, 17 is such that the scan path 13 passes over both reflectors per single sweep.

When operating, the processing system 7 operates the MEM mirror 8 to scan back and forth along the scan path 13. As the beam passes over each of the first and second reflectors 15, 17 a portion of the beam is reflected back and received at the light detector 6b. This results in two pulses being provided to the processing system 7 per scan sweep.

The processing system 7 processes the received pulses to measure longitudinal and lateral distances or displacements. This is performed by triangulation, as will be explained with reference to FIG. 2.

Figure 2:
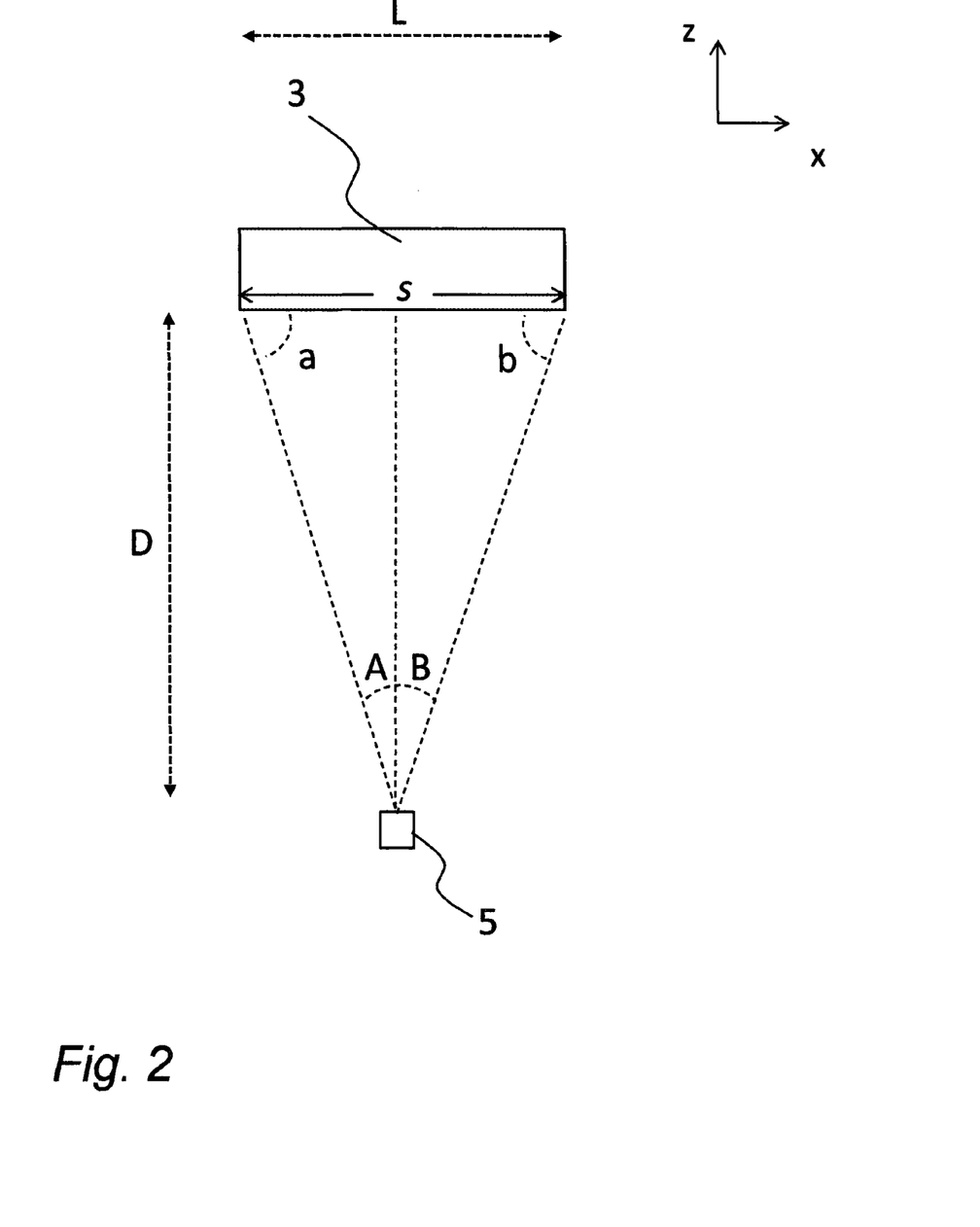
FIG. 2 is a partial plan view of the FIG. 1 diagram which is useful for understanding the invention.

Referring to FIG. 2, which is a schematic top-plan view of the FIG. 1 system, it will be understood that by determining the angles A, B between a reference position and the emitted beam of light which resulted in reflection from the respective reflectors 15, 17, and given the known distance s between the reflectors, elementary trigonometry can be used to determine the z and x axis distances or displacements.

The angles A, B are determined using the position of the MEM mirror 8.

For example, where:
A=angle between the MEM mirror and first reflector 15;
B=angle between the MEM mirror and second reflector 17;
S=known separation distance between reflectors 15, 17;
D=longitudinal (z) distance of the object 3; and
L=lateral (x) distance of the object 3,
then we first correct the angles to account for the fact that they are measured from the MEM mirror 8 rather than the object. So, a=90−A and b=90−B.

Next, D and L are calculated by:

$$D = ((\operatorname{Sin} a \cdot \operatorname{Sin} b)/\operatorname{Sin}(a+b)) \cdot s$$

$$L = \operatorname{Tan} A \cdot D$$

These are of course theoretical equations and in practice one would provide as part of the processing system 7 means for offsetting for calibration and orientation etc. Further, the above calculation is just one of a number of possible mathematical solutions and others can be used to generate the required information from the angles and known separation. The width of the reflectors 15, 17 (a known value) can be used to help determined D, bearing in mind that the closer the object 3 is, the larger the width appears.

In order to determine the angles A, B using the MEM mirror 8 there are a number of options.

One option is to measure the MEM mirror angle directly using feedback, for example optical feedback at the time a reflection pulse is detected from each reflector 15, 17. One such MEM mirror device capable of position feedback is Texas Instruments' product TALP100B described in http://www.ti.com/lit/ds/symlink/talp1000b.pdf although this is a two-dimensional MEM device and a similar one-dimensional MEM can be used. There are a number of feedback mechanisms one could use. For example if the actuation of the mirror is electromagnetic, one could use the back EMF (electro-magnetic flux) from the actuator coil to infer the mirror angle. One could use a hall effect device to do the same. One could use capacitive sensing as well.

Figure 3:
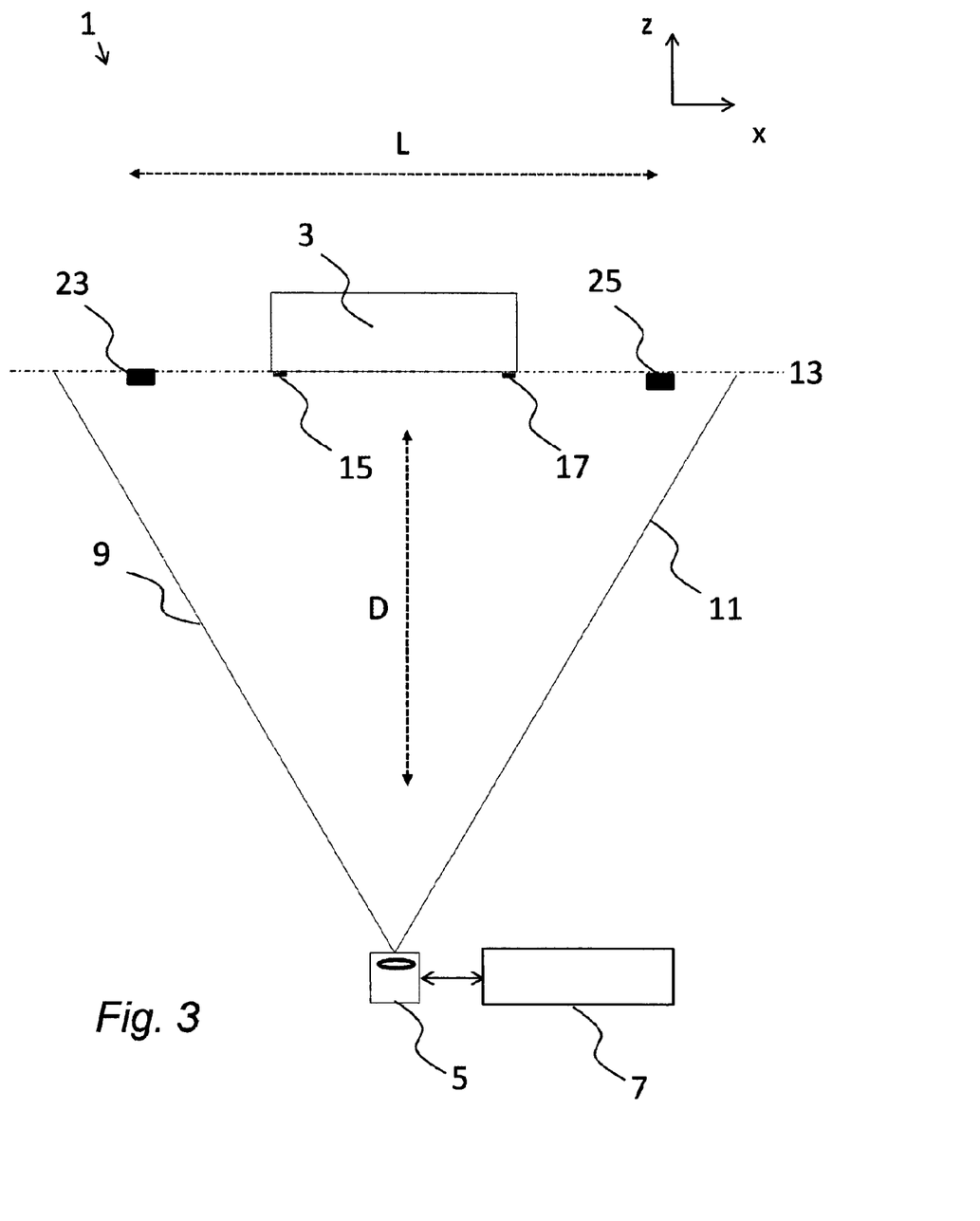
FIG. 3 is a more detailed plan view of the FIG. 1 embodiment including reference reflectors.

A preferred implementation is illustrated schematically in FIG. 3. In this case, one or more reference reflectors 23, 25 is or are positioned within the scan path 13 (note that they are not connected to the object 3) at known position(s) relative to the light source 5/MEM mirror 8. For example, each reference reflector 23, 25 can be positioned at 45 degrees to the MEM mirror. In operation, as the light beam travels along the scan path 13 a proportion of light will be reflected back from the reference reflectors 23, 25 to the detector 6b and the processing system 7 is configured to measure the time taken for the beam to travel from a given reference reflector 23, 25 to each of the object's reflectors 15, 17. This time measurement is calculated based on the known scan time of the MEM mirror 8.

From this, it is straightforward to calculate the angles of each target reflector 15, 17 with a high degree of accuracy. The use of multiple reference reflectors 23, 25 is preferred but only one is necessary. Further information regarding the use of reference reflectors can be obtained from International Patent Application Publication No. WO2011/107112 the contents of which are incorporated herein by reference.

As an alternative to using the first and second reflectors 15, 17, light sensors such as photo detectors can be positioned on the object with the known separation. The scanning system 5 operates in the same way by scanning the light beam along the one-dimensional path using a MEM mirror 8, which path covers the sensors, but in this case the light sensors on the object are employed to inform the processing system 7 of the two points in the scan path when light is detected. The processing system 7 can determine the relevant angles indicated in FIG. 2 using knowledge of the mirror's position at each point in the scan cycle.

Figure 4:
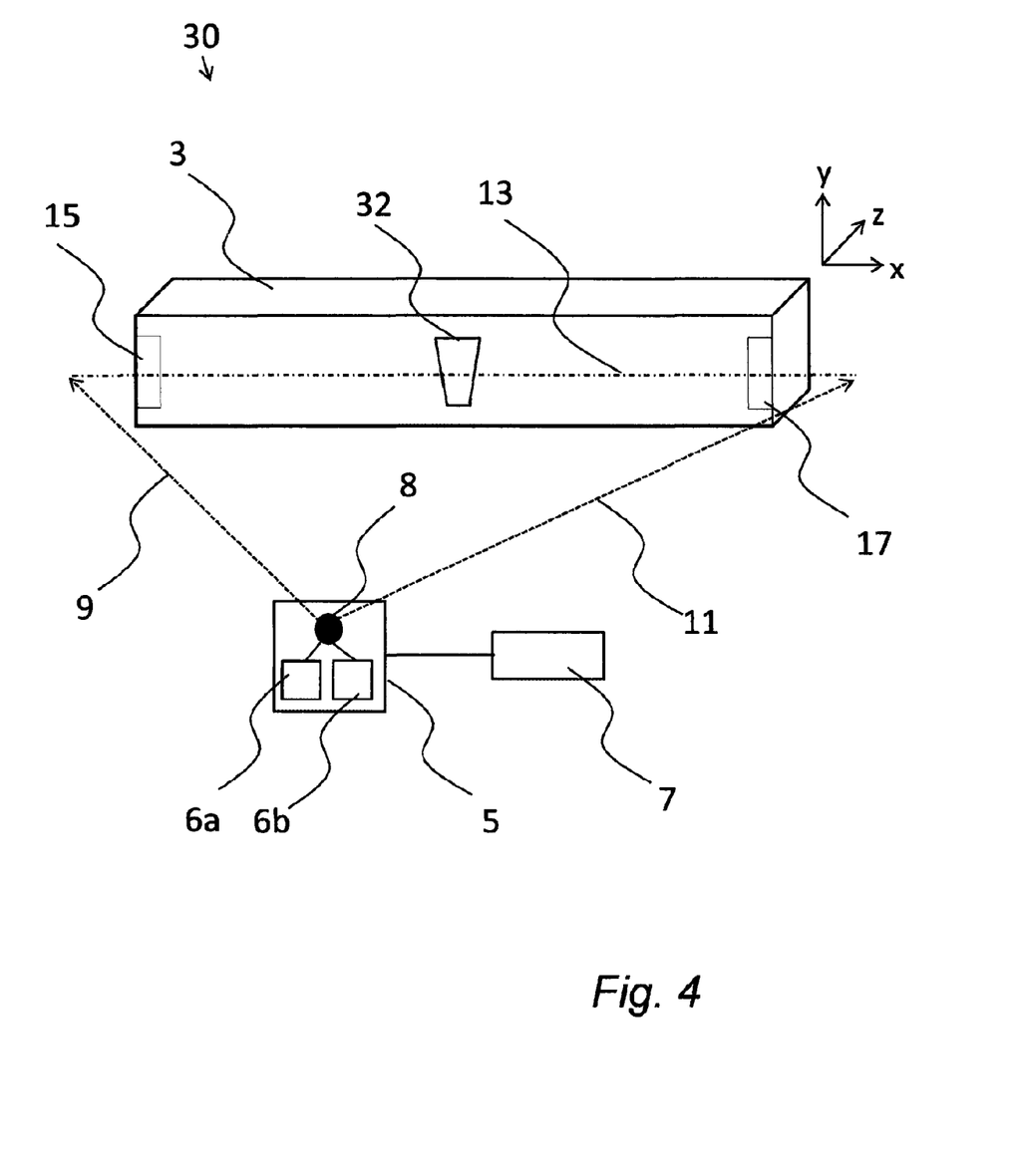
FIG. 4 is a schematic diagram of a further embodiment position determining apparatus according to the invention.

Referring to FIG. 4, a second embodiment apparatus 30 is shown which is capable of position determination in a further, vertical, dimension. The apparatus 30 is largely identical to that of the first 1, but includes the use of a third reflector 32 also fixed to the object 3 in such a way as to be exposed to the light beam and covered by the scan path 13. Here, it is positioned between the first and second reflectors 15, 17.

This third reflector 32 has a property or characteristic that causes the light signal reflected back from it to vary depending on its vertical position, here along the y axis. The processing system 7 is configured to determine from the corresponding reflected pulse what the particular position or displacement is. In this case, the third reflector 32 has a shape or profile that varies along the vertical axis, that is from top to bottom. Particularly, the sides of the shape taper inwards so that it is a trapezoid shape narrowing from top to bottom although in theory only one side need taper. The tapering profile can be reversed so that it narrows in the upwards direction. Either way, the pulse width received is indicative of the vertical position.

Alternative shapes or properties can be used so long as the resulting pulse is indicative of the vertical position of the object 3.

In use, as for the first embodiment, in the second embodiment apparatus 30 light reflected back from the first and second reflectors 15, 17 enables longitudinal and lateral position determination by triangulation; light reflected back from the third reflector 32 results in detection of a pulse whose width varies depending on vertical position of the object. The pulse resulting from the third reflector 32 is distinguished from the others because the pulse width for the former varies whereas the width for the latter ones remains constant.

Figure 5:
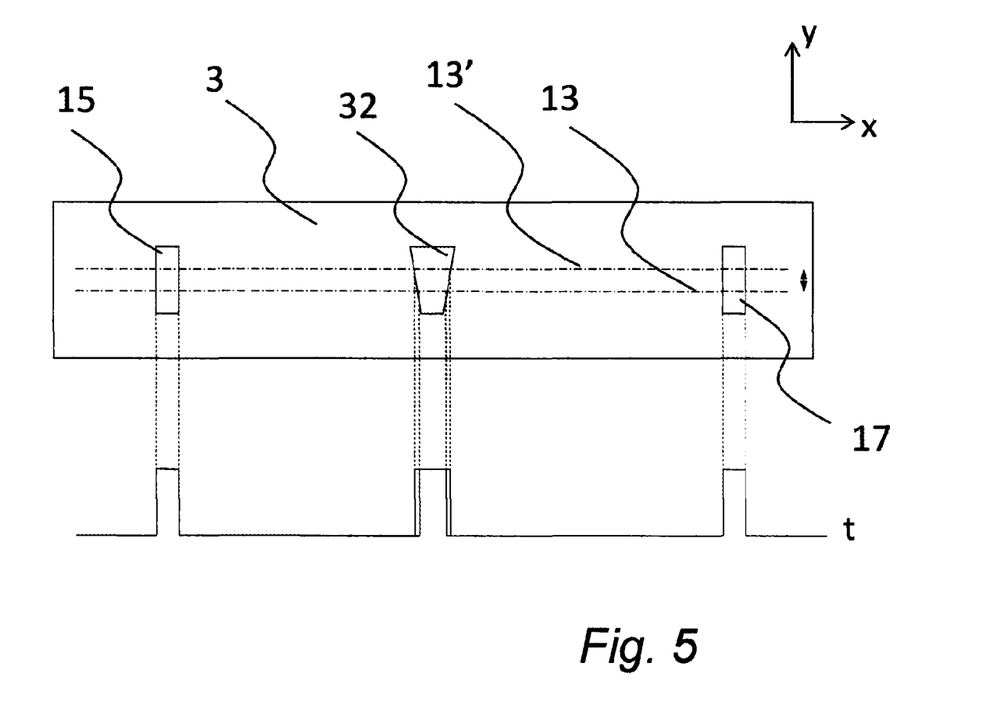
FIG. 5 is a schematic diagram of a front view of the FIG. 4 embodiment with associated waveform.

FIG. 5 shows an example of the waveform produced from a single scan sweep along path 13. The width of the central pulse 34 is indicative of the vertical position of the object 3 along axis y. The processing system 7 is programmed or otherwise configured to determine the vertical position or displacement based on the width of the received pulse. Calibration is required beforehand to correspond the received pulse width to the vertical position. It will be observed that movement of the object 3 downwards causes reflection of light from the subsequent scan path 13 which results in a wider pulse. Movement in the opposite direction results in a narrow pulse.

Although reflector 32 is in the above embodiment provided as a separate, third reflector, in an alternative arrangement one or both of the first and second reflectors 15, 17 can be provided with the required characteristics or properties to cause the reflected light signal to vary depending on relative position. A third reflector is not therefore essential. One or both of the first and second reflectors 15, 17 can have the tapered shape, for example, although for accuracy one would have to detect the centre of the or each reflector 15, 17 rather than relying on the edges.

Also, as already mentioned, the first and second reflectors 15, can be replaced by first and second light sensors which provide direct feedback to the processing system 7 from which the angle of the mirror at each point when light is detected can be determined.

Figure 6:
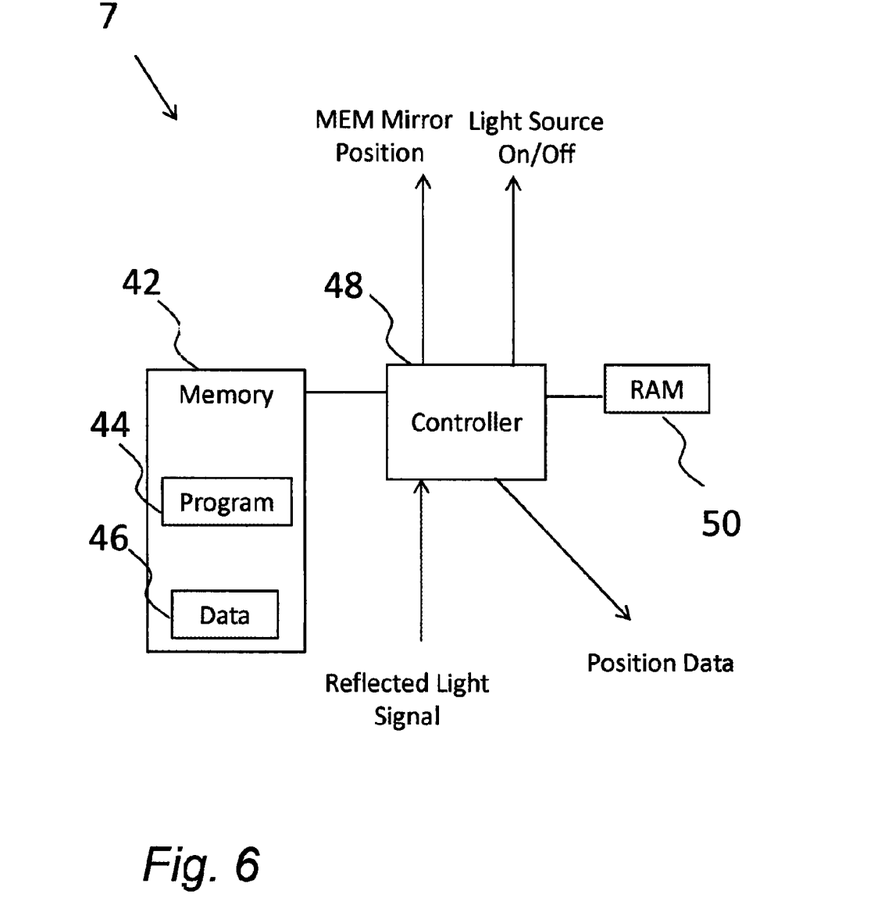
FIG. 6 is a schematic diagram of a processing system of the embodiments.

The processing system 7 in both embodiments may comprise a dedicated processing module, e.g. a microcontroller or FPGA configured to operate under the control of a program. FIG. 6 shows functional components, including a controller 48, RAM 50, a memory 42, an output bus for outputting signals for enabling/disabling the light source 6a, an output bus for outputting signals for controlling the position of the MEM mirror 8, and an input bus for receiving a signal generating by the light detector 6b. An output bus is also provided for outputting the position data, which can be passed to a display device or memory. The position data can be provided in any form, e.g. Cartesian coordinates or a vector representation.

RAM 50 is used by the controller 48 for the temporary storage of data. The memory 42 stores one or more programs having code which, when executed by the controller 48 in conjunction with RAM 50, controls the overall processing system 7. The memory 42 also stores position data 46 representing the appropriate signals to control the MEM mirror 8 through its scan cycle.

Figure 7:
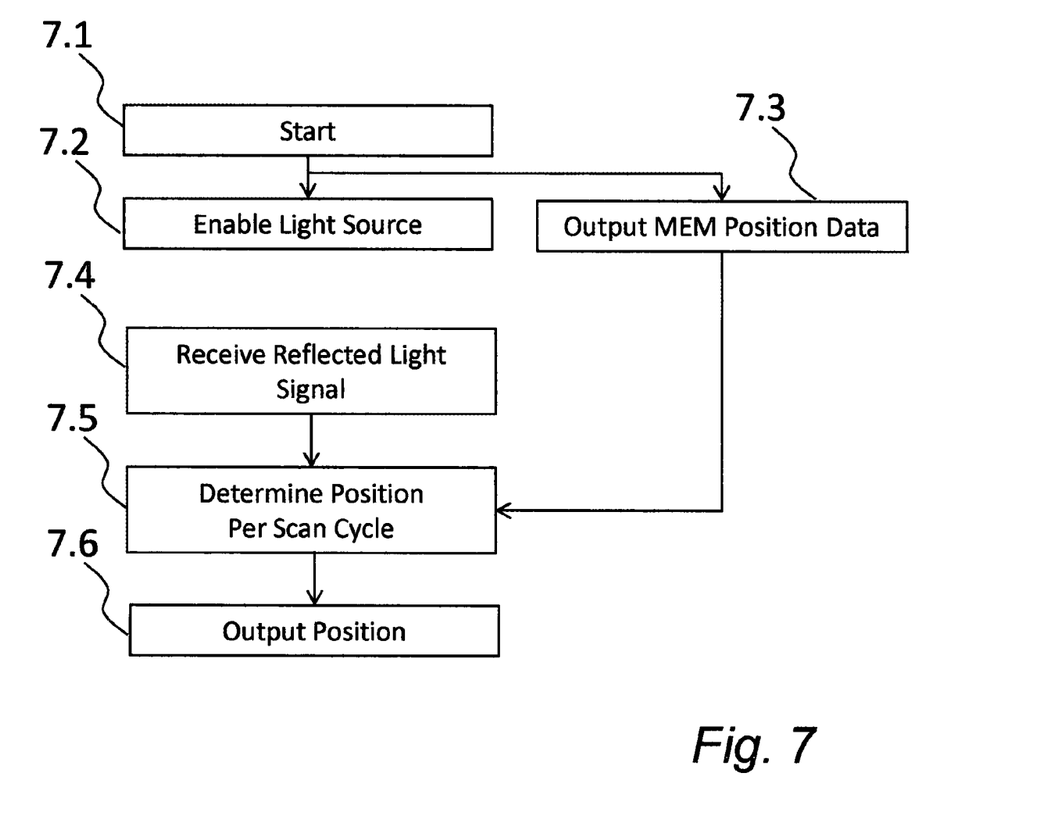
FIG. 7 is a flow diagram indicative of processing steps performed by the FIG. 6 processing system.

Referring to FIG. 7, the main steps performed by the program will now be described in relation to one, one-dimensional scan cycle.

The process starts at step 7.1 which is at the start of a scan cycle. In step 7.2, the light source 6a is turned on (or maintained on) and in step 7.3 position data is output to cause the MEM mirror 8 to scan along its predetermined path 13. In step 7.4, light is received from the light detector 6b. In step 7.5, the position of the object 3 is determined using triangulation or pulse width comparison or a combination of both depending on which dimensional position(s) is or are required. In step 7.6, the position data is output in whichever form is required, e.g. as Cartesian coordinates or a vector representation.

Figure 8:
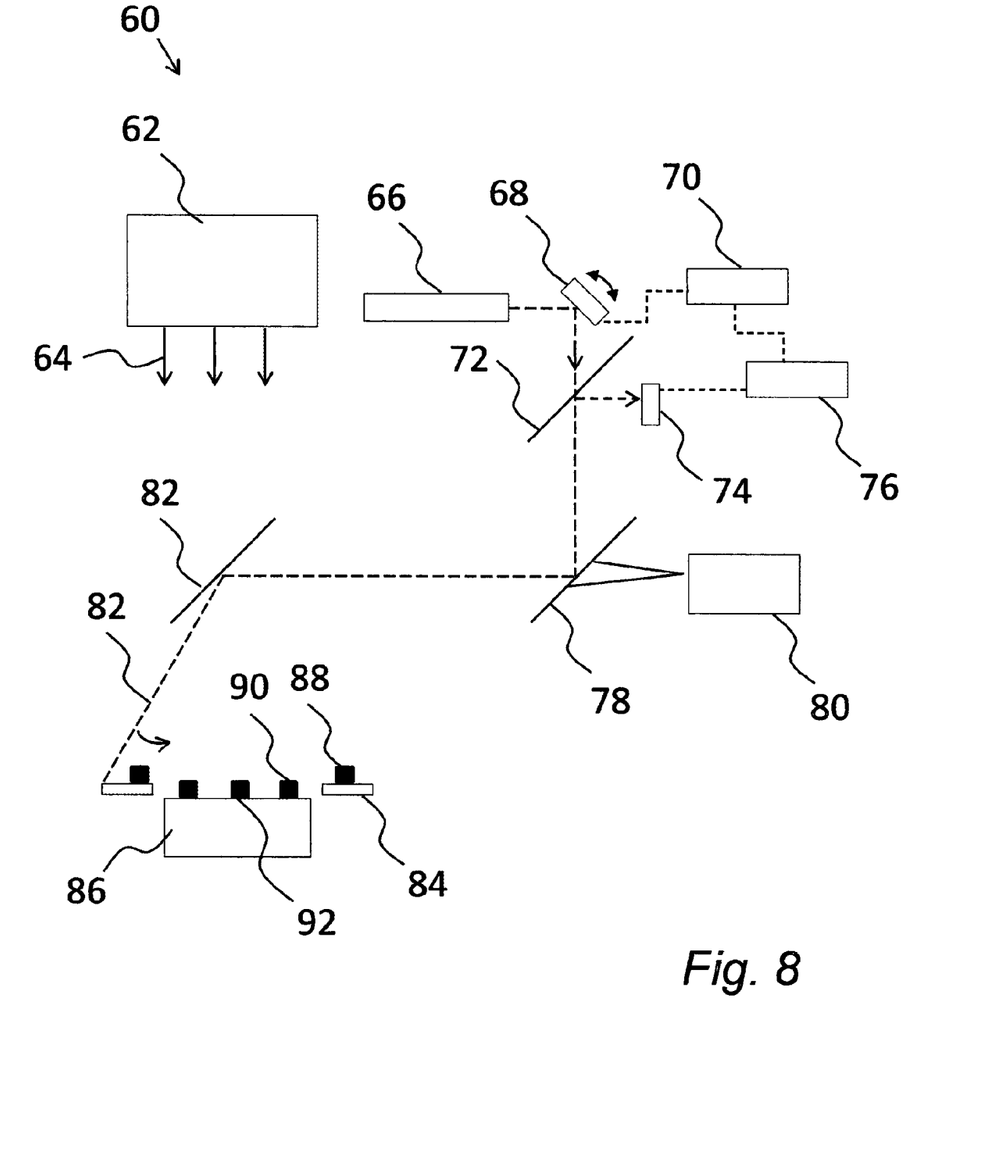
FIG. 8 is a schematic diagram of a further embodiment radiotherapy system according to the invention.

FIG. 8 shows the use of either of the previous embodiments in a radiotherapy system which uses a multi-leaf collimator (MLC). Referring to FIG. 8, a radiation source 62 emits a beam of radiation towards a treatment volume in the downwards direction. The MLC is comprised of a number of leaves the positions of which shape the beam applied to the treatment volume. A single leaf is indicated by the object 86 whose real-time position needs to be determined; the leaf 86 is driven by an electric motor located some distance away and correct operation of the apparatus requires verification of the leaf's position (and indeed that all of leaves of the MLC).

A laser light source 66 is provided, directing its beam 82 towards a one-dimensional MEM scanning mirror 68 controlled by a processing system that includes a position driver module 70. The position driver module 70 operates under computer program control so as to scan the laser beam 82 along a one-dimensional path which passes back and forth over the leaf 86 as well as beyond its extremities.

To direct the beam 82 to the leaf 86 mylar mirrors 78, 82 are provided in a periscope type arrangement. A beam splitter 72 is placed in the path of the beam 82 between the MEM mirror 68 and the first mylar mirror 78. The beam splitter 72 directs a portion of the light returned from the leaf 86 to a photo sensor 74 which detects the returning light and passes the resulting signal to another part of the processing system, which determines position.

Module 80 is a field lamp 24 which emits a light beam which is incident on the rear of one of the mylar mirrors 78 through which at least part of the beam is transmitted. This light beam then falls on the mirror 28 and is directed towards the treatment volume. The light source 66 and field lamp 80 are positioned relative to the radiation source 62 and mirrors 78, 82 so that they are in a location that is optically identical to that of the radiation source 62 and so illuminates the treatment volume in the same manner as the radiation.

As before, on top of the (and indeed each) leaf 86 of the MLC are provided a pair of retro-reflectors 90 at a known separation distance s. Also provided is a third retro-reflector 92 which, like that provided in the second embodiment, has a shape that varies along a given axis or plane so that light reflected from it produces a detectable beam that varies depending on its position along or parallel with said plane.

Thus, the apparatus 60 is capable of determining the leaf's position in one or two dimensions using the pair of retro reflectors 60 in the same way as the first embodiment. Reference retro-reflectors 88 are shown fixed on supports 84 either side of the MLC leaves and outside their field of travel; these enable calculation of the mirror angles as described in the first embodiment. Additionally, or alternatively, the position in a further dimension is determined using the third retro-reflector 92 in the same way as the second embodiment.

Also, as already mentioned, the first and second reflectors 90 can be replaced by first and second light sensors which provide direct feedback to the processing system 7 from which the angle of the mirror at each point when light is detected can be determined.

In all embodiments, it will be appreciated that in practice the relevant position of the MEM mirror is that which existed a few nanoseconds before the light is received, to allow for travel time. This is unlikely to make a significant difference.

In a fourth embodiment, not shown in the Figures, the first and second reflectors 15, 17, 90 as described in the previous embodiments can be replaced with first and second light sources, for example infra-red light sources, located on the object and which are separated by a known distance. The scanning system 5 operates in the same way as before with a light sensor associated with said scanning system detecting the first and second points in the MEM mirror's one-dimensional scanning cycle at which light from each source is detected after reflection by the MEM mirror. Given these two points in the scan cycle, the processing system 7 can then determine the angles indicated in FIG. 2 in order to determine the object's position. This principle is outlined in http://adriaticresearch.org/Research/pdf/Tracking_OMEMS2008.pdf (see FIG. 1(c)) although in this document only one light source is used and two mirrors are required. In the present embodiment, we employ two light sources of known separation on the object and require only one, one-dimensional MEM mirror and one light sensor.

In all embodiments, there may also be provided a module for calibrating the motion of the MEM mirror within each scan cycle. Additional reference mirrors may be provided for this purpose, as described in WO 2011/107112.

An exemplary embodiment provides a system and method for determining the position of an object, which is less complex and/or expensive to implement than current methods.

It will be appreciated that the above described embodiments are purely illustrative and are not limiting on the scope of the invention. Other variations and modifications will be apparent to persons skilled in the art upon reading the present application.

Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. An apparatus for position-detection of an object within a region, the apparatus comprising:
   first and second target elements mounted or mountable on an object and having a known separation distance between the first and second target elements;
   a scanning light source adapted to issue a beam of light along a one-dimensional scanning path, which illuminates a point that moves over the first and second target elements, wherein the scanning light source comprises a source of light and a mirror, the source of light being directed towards the mirror, the mirror being controllably movable so as to direct light from the source towards the object along the one-dimensional scanning path;
   at least one light detector, arranged to detect light reflected from, or received by, the first and second target elements;
   a processor; and
   a non-transitory computer-readable medium comprising a computer program stored thereon, which when executed by the processor configures the processor to determine the position of the object within the region based on:
   first and second points in the scanning path at which the at least one light detector detects light returned from, or received by, the first and second target elements;
   respective first and second angles between a reference position and positions of said first and second points in the scanning path; and
   the known separation distance between the first and second target elements,
   wherein the processor is configured by the computer program to determine the first and second angles using optical feedback to directly measure the angle at which the scanning light source is emitting its beam when a reflection from at least one of the first or second reflective elements is detected at the at least one light detector, and wherein the processor is configured by the computer program to determine the first and second angles using optical or electrical feedback to directly measure the angle of the mirror when a reflection from at least one of the first or second reflective elements is detected at the at least one light detector.

2. The apparatus according to claim 1, wherein the first and second target elements are reflective elements.

3. The apparatus according to claim 2, wherein the processor is configured to determine the first and second angles using optical feedback to directly measure the angle at which the scanning light source is emitting its beam when a reflection from at least one of the first or second reflective elements is detected at the at least one light detector.

4. The apparatus according to claim 2, further comprising one or more reference reflectors located at known position(s) within the region covered by the scanning path and wherein the processor is configured to determine the first and second angles based on the respective positions of said first and second points relative to reference point(s) in the scanning path at which the at least one light detector detects light returned from the or each reference reflector.

5. The apparatus according to claim 2, wherein the processor is configured to determine an indication of at least the object's distance from the light source along a first dimensional axis by triangulation based on the first and second angles and the known separation distance between the first and second reflective elements.

6. The apparatus according to claim 5, wherein the processor is further configured to generate an indication of the object's relative position along a second dimensional axis, generally orthogonal to the first dimensional axis.

7. The apparatus according to claim 1, wherein the source of light is a laser.

8. The apparatus according to claim 1, wherein the mirror is part of a micro-electromechanical (MEM) device with an associated controller.

9. The apparatus according to claim 1, wherein the first and second target elements are reflective elements, and wherein the at least one light detector is configured so as to receive the reflected light from the controllably movable mirror.

10. The apparatus according to claim 2, wherein one of the first or second reflective elements, or a further reflective element, is provided having a property or characteristic that causes a temporal variation in reflected light depending on the part of the element that is illuminated along a given axis, and wherein the processor is further configured to determine the position of the object based on the reflected light received by the detector from said reflective element.

11. The apparatus according to claim 10, wherein said one of the first or second reflective elements or said further reflective element has a shape that varies in width along the given axis, transverse to the one-dimensional scanning path, and wherein the processor is further configured to determine the position of the object based on the width of the light pulse received by the at least one light detector from said reflective element.

12. The apparatus according to claim 11, wherein said reflective element has a shape that tapers inwards along the given axis.

13. Radiotherapeutic apparatus including a position determination apparatus according to claim 1.

14. A method for position-detection of an object within a region, the method comprising:
   scanning a beam of light from a light source along a one-dimensional scanning path, which illuminates a point that moves over first and second target elements mounted on an object separated by a known distance, wherein the scanning light source comprises a source of light and a mirror, the source of light being directed towards the mirror, the mirror being controllably movable so as to direct light from the source towards the object along the one-dimensional scanning path;
   detecting by a detector light reflected from, or received by, the first and second target elements; and
   determining the position of the object within the region based on first and second points in the scanning path at which the detector detects light returned from, or received by, the first and second target elements, respective first and second angles between a reference position and positions of said first and second points in the scanning path, and the known separation distance between the first and second target elements, including determining the first and second angles using optical feedback to directly measure the angle at which the scanning light source is emitting its beam when a reflection from at least one of the first or second reflective elements is detected at the detector, and determining the first and second angles using optical or electrical feedback to directly measure the angle of the mirror when a reflection from at least one of the first or second reflective elements is detected at the detector.

15. The method according to claim 14, wherein determining the position of the object comprises determining the position of a movable object within a radiotherapeutic apparatus.

16. An apparatus for position-detection of an object within a region, the apparatus comprising:
- first and second reflective elements mounted or mountable on an object and having a known separation distance between the first and second reflective elements, wherein at least one of the first or second reflective elements, or a further reflective element, is provided having a property or characteristic that causes a temporal variation in reflected light depending on the part of the element that is illuminated along a given axis;
- a scanning light source adapted to issue a beam of light along a one-dimensional scanning path, which illuminates a point that moves over the first and second reflective elements, wherein said at least one of the first or second reflective elements or said further reflective element has a shape that varies in width along the given axis, transverse to the one-dimensional scanning path;
- at least one light detector, arranged to detect light reflected from the first and second reflective elements;
- a processor; and
- a non-transitory computer-readable medium comprising a computer program stored thereon, which when executed by the processor configures the processor to determine the position of the object within the region based on:
- first and second points in the scanning path at which the at least one light detector detects light returned from the first and second reflective elements;
- a width of a pulse of the light received by the at least one light detector from the at least one of the first or second reflective elements, or the further reflective element, that causes a temporal variation in the reflected light; and
- the known separation distance between the first and second reflective elements.

* * * * *